United States Patent

Skuballa et al.

[11] Patent Number: 5,880,126
[45] Date of Patent: Mar. 9, 1999

[54] 9H-PYRIDU ((3,4-B) INDOLE DERIVATIVES

[75] Inventors: Werner Skuballa, Berlin; Bernd Buchmann, Hohen Neuendorf; Hartmut Rehwinkel, Berlin; Frank Schneider, Berlin; Wolfgang Fröhlich, Berlin; Claudia Giesen, Berlin; Hartwig Hennekes, Berlin, all of Germany

[73] Assignee: Schering Aktiengesellschaft, Germany

[21] Appl. No.: 875,090

[22] PCT Filed: Jan. 19, 1996

[86] PCT No.: PCT/EP96/00213

§ 371 Date: Dec. 8, 1997

§ 102(e) Date: Dec. 8, 1997

[87] PCT Pub. No.: WO96/22989

PCT Pub. Date: Aug. 1, 1996

[30] Foreign Application Priority Data

Jan. 23, 1995 [DE] Germany ......... 195 02 753.1

[51] Int. Cl.$^6$ ......... A61K 31/495; A61K 31/44; C07D 401/06; C07D 471/04

[52] U.S. Cl. ......... 514/253; 514/292; 544/361; 546/85; 546/86

[58] Field of Search ......... 546/85, 86; 544/361; 514/292, 253

[56] References Cited

U.S. PATENT DOCUMENTS

| | | | |
|---|---|---|---|
| 4,719,210 | 1/1988 | Seidelmann et al. | 514/222 |
| 5,414,002 | 5/1995 | Biere et al. | 514/292 |
| 5,506,234 | 4/1996 | Huth et al. | 514/292 |

FOREIGN PATENT DOCUMENTS

| | | |
|---|---|---|
| 4223164 | 1/1993 | Germany . |
| 950509 | 2/1964 | United Kingdom . |

*Primary Examiner*—Laura L. Stockton
*Attorney, Agent, or Firm*—Miller, White, Zelano, & Branigan, P.C.

[57] ABSTRACT

9H-Pyrido[3,4-b]indole compounds have a pronounced leukotriene-$B_4$ antagonistic action, and thus show a completely different spectrum of activity than known β-carbolines.

4 Claims, No Drawings

9H-PYRIDU ((3,4-B) INDOLE DERIVATIVES

SUMMARY OF THE INVENTION

This application is a 377 of PCT/EP96/00213 filed Jan. 19, 1996. The invention relates to new 9H-pyrido[3,4-b] indole derivatives of general formula I

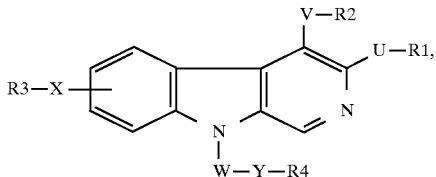

in which

U, V and W mean a carbon-carbon bond or a $C_1$–$C_6$ alkylene group, $R_1$ represents a hydrogen atom, a hydroxy group or a carboxyl group, and $R_2$ symbolizes a hydrogen atom, a hydroxy group, a $C_1$–$C_4$ alkoxy group, a $C_1$–$C_6$ alkanoyloxy group or a $C_1$–$C_4$-ω-carboxyalkoxy group, or $R_1$ and $R_2$ together are an oxycarbonyl group, and in which X means a carbon-carbon bond or an oxygen, Y means a carbon-carbon bond, the grouping —CONR' with R' in the meaning of a hydrogen atom or a $C_1$–$C_7$ alkyl group that is optionally substituted by a carboxyl group, or the grouping

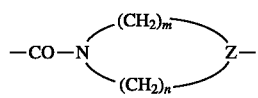

with m and n in the meaning of numbers of a total of 3, 4 or 5, and Z in the meaning of a methylidine group or an aza group, and $R_3$ and $R_4$ in each case symbolize a phenyl group optionally substituted by halogen atoms, trifluoromethyl groups, cyanide groups, $C_1$–$C_7$ alkyl groups, $C_1$–$C_4$ alkoxy groups, carboxyl groups and/or nitro groups; $C_1$–$C_4$ alkylenephenyl group or naphthyl group, and in the case of carboxylic acids of general formula I, also their esters of physiologically harmless alcohols, their amides of physiologically tolerable amines and their salts of physiologically compatible bases.

The 9H-pyrido[3,4-b]indole derivatives of general formula I according to the invention are derivatives of the 9H-pyrido[3,4-b]indole derivatives, known a priori and often also referred to as β-carbolines, of general formula II

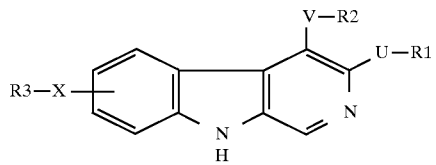

in which

U, V, X, $R_1$, $R_2$ and $R_3$ have the above-mentioned meaning, which are pharmacologically active substances that affect the central nervous system and can be used as active ingredients in psychopharmaceutical agents (EP-A 0054 507 and EP-A 0239 669).

It has now been found that the 9H-pyrido[3,4-b]indole derivatives of general formula I according to the invention have, surprisingly enough, a pronounced leukotriene-$B_4$ antagonistic action, and thus show a completely different spectrum of activity than the substances of general formula II known a priori.

Relative to their pharmacological action and their therapeutic applicability, the compounds according to the invention with their chemical structure are comparable to completely different substances known a priori, such as, for example, the cycloalkane derivatives known a priori from WO 92/16504, WO 93/11105, DE-A 42 27 790 or DE-A 42 42 390; the phenyl derivatives known a priori from WO 94/04522; the naphthyl derivatives known a priori from WO 92/05145,; the pyridine derivatives known a priori from WO 91/14676 and WO 94/02464; and the indole derivatives known a priori from WO 92/04321.

The 9H-pyrido[3,4-b]indole derivatives of general formula I according to the invention can have as substituent $R_2$, for example, a methoxy group, an ethoxy group, a tert-butyloxy group, an acetoxy group or a benzoyloxy group and/or as substituents $R_3$ and/or $R_4$ a phenyl radical, benzyl radical or phenyl radical optionally substituted in o-, m- or p-position by a $C_1$–$C_4$ alkyl group (such as, for example, the methyl group), a $C_1$–$C_4$ alkoxy group (such as, for example, the methoxy group, a chlorine atom, a fluorine atom, a trifluoromethyl group, a carboxyl group or a nitro group.

Of the 9H-pyrido[3,4-b]indole derivatives of general formula I according to the invention, in the trials hitherto performed, especially the following substance groups were studied:

a) Compounds of general formula I with U in the meaning of a carbon-carbon bond, and in the latter preferably those whose substituent $R_1$ is a carboxyl group, their esters, amides or salts.

b) Compounds of general formula I with V in the meaning of a methylene group and, among the latter, preferably compounds with $R_2$ in the meaning of a hydrogen atom, an alkoxy group, such as, for example, the methoxy group or an alkanoxy group such as the acetoxy group.

c) Compounds of general formula I with X in the meaning of an oxygen atom and $R_3$ in the meaning of an optionally substituted phenyl group or benzyl group.

d) Compounds of general formula I with W in the meaning of a $C_1$–$C_6$ alkylene group, Y in the meaning of an N-alkylcarbanoyl group and $R_4$ in the meaning of an optionally substituted $C_1$–$C_7$ alkylenephenyl group.

e) Substances of general formula I with W in the meaning of a $C_1$–$C_6$ alkylene group, Y in the meaning of an N-carboxymethyl-carbanoyl group and $R_4$ in the meaning of an optionally substituted $C_1$–$C_4$ alkylenephenyl group and f) Substances of general formula I with W in the meaning of an N-carbonylpiperazino group and $R_4$ in the meaning of an optionally substituted $C_1$–$C_4$ alkylenephenyl group.

g) Compounds of general formula I with $R_3$ and/or $R_4$ in the meaning of a phenyl group, a p-nitrophenyl group, a benzyl group or a phenethyl group.

Within the framework of the hitherto performed trials, special attention was focussed on the compounds that in addition to features d, e or f also have all the features of groups a to c and g.

Carboxylic acids of general formula I can be esterified according to the invention with physiologically harmless alcohols. Such alcohols are, for example, alkanols with 1 to 6 carbon atoms, such as methanol, ethanol, propanol, isopropanol, butanol, sec-butanol or tert-butanol or cycloalkanols with up to 7 carbon atoms, such as cyclopentanol or cyclohexanol. On the other hand, they can also be amidated with amines according to the invention. In addition to ammonia itself, suitable amines are $C_1$–$C_6$ alkylamines, such as methylamine, ethylamine or isopropylamine, $C_1$–$C_6$ dialkylamines such as dimethylamine, diethylamine or diisopropylamine or saturated N-heterocycles such as pyrrolidine, piperidine, N-methylpiperidine, piperazine or morpholine. For salt formation of the carboxylic acids of general formula I according to the invention, all physiologically compatible inorganic or organic bases that are usually used for the production of pharmacologically active carboxylic acid salts are suitable. Such bases are, for example, alkali metal hydroxides, alkaline-earth metal hydroxides, alkali metal carbonates, alkaline-earth metal carbonates such as sodium hydroxide, sodium bicarbonate, sodium carbonate, potassium hydroxide, potassium carbonate, calcium hydroxide or calcium carbonate. On the other hand, suitable bases are also ammonia or amines such as methylamine, diethylamine, cyclohexylamine, ethanolamine, diethanolamine, triethanolamine, N-methylglucamine, morpholine or tris-(hydroxymethyl)-methylamine.

The 9H-pyrido[3,4-b]indole derivatives of general formula I according to the invention can be produced, for example, in a way known in the art from the 9H-pyrido[3,4-b]indole derivatives of general formula II known a priori, by the latter being alkylated with a reactive compound of general formula III

$$Q\text{—}W\text{—}Y\text{—}R_4 \qquad (III),$$

in which W, Y and $R_4$ have the above-mentioned meaning and Q symbolizes a nucleofuge radical, and the compounds obtained are optionally converted into their esters, amides or salts.

Suitable nucleofuge radicals Q are, for example, the acyl radicals of stronger carboxylic acids, such as trifluoroacetic acid, sulfonic acid radicals such as those of methanesulfonic acid, trifluoromethanesulfonic acid, benzenesulfonic acid or p-toluenesulfonic acid and especially the halogen atoms chlorine, bromine and iodine.

The conditions under which the alkylation of 9H-pyrido[3,4-b]indole derivatives of general formula II is carried out are the same that are otherwise also used for alkylating amines and require no explanation. Also, the optionally subsequent esterification of the free carboxylic acids or alcohol and the optional amide formation from the free carboxylic acids is carried out under conditions that are familiar to each one skilled in the art.

It was already mentioned that the new alkylated 9H-pyrido[3,4-b]indole derivatives have a pronounced leukotriene-$B_4$-antagonistic activity. Consequently, they are active in an antiinflammatory, antiallergic and antiproliferative manner.

The physiological and especially the pathophysiological importance of leukotriene $B_4$ is summarized in several new works: a) The Leukotrienes, Chemistry and Biology, eds., L. W. Chakrin, D. M. Bailey, Academic Press 1984. b) J. W. Gillard et al., Drugs of the Future 12, 453 (1987). c) B. Samuelson, Sciences 237, 1171 (1987). d) C. W. Parker, Drug Development Research 10, 277 (1987). It follows from the above that $LTB_4$ is a more important inflammation mediator for inflammatory diseases, in which leukocytes invade the diseased tissue.

The effects of $LTB_4$ are triggered on the cellular plane by the binding of $LTB_4$ to a specific receptor.

It is known concerning $LTB_4$ that it causes the adhesion of leukocytes to the blood vessel wall. $LTB_4$ is chemotactically active, i.e., it triggers a directed migration of leukocytes in the direction of a gradient of increasing concentration. In addition, based on its chemotactic activity, it indirectly alters vascular permeability, whereby a synergism with prostaglandin $E_2$ is observed. $LTB_4$ obviously plays a decisive role in inflammatory, allergic and immunological processes.

Leukotrienes and especially $LTB_4$ are involved in skin diseases that accompany inflammatory processes (increased vascular permeability and formation of edemas, cell infiltration), increased proliferation of skin cells and itching, such as, for example, in eczemas, erythemas, psoriasis, pruritus and acne. Pathologically increased leukotriene concentrations are either causally involved in the development of many dermatides or there is a connection between the persistence of the dermatides and the leukotrienes. Considerably increased leukotriene concentrations were measured in, for example, the skin of patients with psoriasis, atopic dermatitis, allergic contact dermatitis, bullous pemphigoids, delayed pressure urticaria and allergic vasculitis.

Leukotrienes and especially $LTB_4$ are also involved in diseases of internal organs, for which an acute or chronically inflammatory component was described, e.g., arthropathies (rheumatic arthritis); diseases of the respiratory tract (asthma and chronically obstructive lung diseases (OPD)); inflammatory intestinal diseases (ulcerous colitis and Crohn's disease), as well as damage after reperfusion (of heart, intestinal or kidney tissue), which develop by, at times, pathological obstruction of blood vessels, such as glomerulonephritis, NSAID gastropathies, multiple sclerosis, rhinitis and inflammatory eye diseases.

Leukotrienes and especially $LTB_4$ are also involved in the disease of multiple sclerosis and in the clinical appearance of shock (triggered by infections, burns or in complications in kidney dialysis or other perfusion techniques that are discussed separately).

Leukotrienes and especially $LTB_4$ also have an effect on the formation of white blood cells in the bone marrow, on the growth of unstriped muscle cells, of keratinocytes and of B-lymphocytes. $LTB_4$ is therefore involved in diseases with inflammatory processes and in diseases with pathologically increased formation and growth of cells.

For example, leukemia or arteriosclerosis represent diseases with this appearance.

By the antagonization of effects especially of $LTB_4$, the active ingredients and their form of administration of this invention are specific medicines in the diseases of humans and animals, in which especially leukotrienes play a pathological role.

They are suitable in combination with the additives and media that are commonly used in galenical pharmaceutics for local treatment of diseases of the skin, in which leukotrienes play an important role, for example, contact dermatitis, eczemas of the most varied type, neurodermatoses, erythrodermia, pruritus vulvae et ani, rosacea, erythematosus cutaneous, psoriasis, lichen ruber planus et verrucosus and similar skin diseases.

In addition, the new compounds are suitable for treating multiple sclerosis and the symptoms of shock.

The production of the pharmaceutical agent specialties is carried out in the usual way by the active ingredients being converted with suitable additives into the desired form of administration, such as, for example: solutions, ointments, creams or plasters.

In the pharmaceutical agents that are thus formulated, the active ingredient concentration depends on the form of administration. In the case of lotions and ointments, an active ingredient concentration of 0.0001% to 3% is preferably used.

Moreover, the new compounds optionally in combination with the commonly used vehicles and adjuvants are also well-suited for the production of inhalants, which can be used for the treatment of allergic diseases of the respiratory system, such as, for example, bronchial asthma or rhinitis.

The new substances are also suitable in the form of capsules, tablets or coated tablets, which preferably contain 0.1 to 100 mg of active ingredient and are administered orally or in the form of suspensions that preferably contain 1–200 mg of active ingredient per dosage unit and are administered rectally even for treating diseases of the internal organs, in which leukotrienes play an important role, such as, e.g.: diseases of the intestinal tract, such as colitis ulcerosa and colitis granulomatosa.

In these new forms of administration, in addition to the treatment of diseases of internal organs with inflammatory processes, the new compounds are also suitable for the treatment of diseases in which, depending on the leukotriene, the increased growth and the new formation of cells are emphasized. Examples are leukemia (increased growth of white blood cells) or arteriosclerosis (increased growth of unstriped muscle cells of blood vessels.)

The new 9H-pyrido[3,4-b]indole derivatives can also be used in combination, such as, e.g., with lipoxygenase inhibitors, cyclooxygenase inhibitors, glucocorticoids, prostacyclin agonists, thromboxane antagonists, leukotriene-$C_4$ antagonists, leukotriene-$D_4$ antagonists, leukotriene-$E_4$ antagonists, leukotriene-$F_4$ antagonists, phosphodiesterase inhibitors, calcium antagonists, PAF antagonists or other known forms of treatment of the respective diseases.

The embodiments below are used for a more detailed explanation of the process according to the invention.

EXAMPLE 1

998 mg of 6-benzyloxy-4-methoxymethyl-9H-pyrido[3,4-b]indole-3-carboxylic acid-1-methylethyl-ester (2.4 mmol) is introduced into 10 ml of dry tetrahydrofuran and deprotonated at 0° C. with 72 mg of sodium hydride (80% suspension in oil) (2.4 mmol). Then, it is stirred for 20 minutes at room temperature, mixed with 630 mg of 2-[N-methyl-N-(2-phenylethyl)-amino]-2-bromoacetamide (2.4 mmol)—dissolved in 10 ml of tetrahydrofuran—stirred for another 5 hours at room temperature, filtered on diatomaceous earth, and then the solvent is drawn off in a vacuum. The crude product that is obtained is recrystallized from dichloromethane/diethyl ether, and 1.22 g of 6-benzyloxy-4-methoxymethyl-9-{2-[N-methyl-N-(2-phenylethyl) amino]-2-oxoethyl}-9H-pyrido-[3,4-b]indole-3-carboxylic acid-(1-methyl-ethyl)-ester is obtained.

IR=2980, 2940, 1710, 1650, 1480, 1450, 1300, 1190, 1100 $cm^{-1}$.

EXAMPLE 2

211 mg of 6-benzyloxy-4-methoxymethyl-9-{2-[N-methyl-N-(2-phenylethyl)-amino]-2-oxoethyl}-9H-pyrido [3,4-b]indole-3-carboxylic acid-(1-methylethyl)-ester is mixed in 1 ml of methanol with 0.5 ml of aqueous 2N sodium hydroxide solution and held at 40° C. until the reaction is completed. Then, the reaction mixture is acidified with dilute hydrochloric acid, the precipitated yellow reaction product is suctioned off, washed with water and diethyl ether and dried in a vacuum. 150 mg of 6-benzyloxy-4-methoxymethyl-9-{2-[N-methyl-N-(2-phenylethyl)-amino]-2-oxoethyl}-9H-pyrido[3,4-b]indole-3-carboxylic acid is obtained.

IR=3400, 2940, 1650, 1610, 1570, 1480, 1380, 1360, 1200 $cm^{-1}$.

EXAMPLE 3

2.63 g of 6-benzyloxy-4-methoxymethyl-9H-pyrido[3,4-b]indole-3-carboxylic acid-(1-methyl-ethyl)-ester (6.5 mmol) is taken up in 50 ml of dry tetrahydrofuran and mixed for deprotonation with 235 mg of 80% sodium hydride suspension in oil (7.1 mmol). It is allowed to stir for 20 more minutes at room temperature, then 2.22 g of 6-[N-methyl-N-(2-phenylethyl)-amino]-2-oxohexylbromide (7.1 mmol)—dissolved in 10 ml of tetrahydrofuran—is added. It is stirred for 12 hours at room temperature, mixed with 5 ml of 2N aqueous hydrochloric acid and diluted with water. It is then extracted with dichloromethane, the solvent is drawn off in a vacuum, and the crude product that is obtained is chromatographed on silica gel using hexane-ethyl acetate. 4.1 g of 6-benzyloxy-4-methoxymethyl-9{6-[N-methyl-N-(2-phenylethyl)-amino]-2-oxohexyl}9H-pyrido[3,4-b] indole-3-carboxylic acid-(1-methylethyl)-ester is obtained as a brownish oil.

IR=3340, 2980, 2930, 1710, 1640, 1580, 1480, 1450, 1370, 1310 $cm^{-1}$.

EXAMPLE 4

350 mg of 6-benzyloxy-4-methoxymethyl-9-{6-[N-methyl-N-(2-phenylethyl)-amino]-2-oxohexyl}-9H-pyrido [3,4-b]indole-3-carboxylic acid-(1-methylethyl)-ester (0.55 mmol) is mixed in 10 ml of methanol with 1 ml of 2N aqueous sodium hydroxide solution and held at 40° C. until the reaction is completed. Then, the reaction mixture is acidified with dilute hydrochloric acid, and the precipitated product is suctioned off. It is washed with water and then with diethyl ether, dried in a vacuum, and 212 mg of 6-benzyloxy-4-methoxymethyl-9-{6-[N-methyl-N-(2-phenylethyl)-amino]-2-oxohexyl}-9H-pyrido-[3,4-b]-indole-3-carboxylic acid is obtained as a yellow, amorphous powder.

IR=3480, 3060, 3020, 2930, 1740, 1650, 1610, 1580, 1480, 1450, 1370, 1330 $cm^{-1}$.

EXAMPLE 5

1000 mg of 5-benzyloxy-4-methoxymethyl-9H-pyrido[3,4-b]indole-3-carboxylic acid-1-methylethyl-ester (2.5 mmol) is introduced into 10 ml of dry tetrahydrofuran and deprotonated at 0° C. with 72 mg of sodium hydride (80% suspension in oil) (2.4 mmol). Then, it is stirred for 20 minutes at room temperature, mixed with 617 mg of 2-[N-methyl-N-benzyl]-2-bromoacetamide (2.5 mmol)—dissolved in 3 ml of tetrahydrofuran—stirred for another 12 hours at room temperature, filtered on diatomaceous earth, and then the solvent is drawn off in a vacuum. The crude product that is obtained is chromatographed on hexane-ethyl acetate, and 890 mg of 5-benzyloxy-4-methoxymethyl-9-{2-[N-methyl-N-benzylamino]-2-oxoethyl}-9H-pyrido[3,4-b]indole-3-carboxylic acid-(1-methyl-ethyl)-ester is obtained as an amorphous powder with a melting point of 155°–157° C.

IR=2978, 1734, 1653, 1503, 1467, 1268, 1104 $cm^{-1}$.

EXAMPLE 6

460 mg of 5-benzyloxy-4-methoxymethyl-9-{2-[N-methyl-N-benzyl-amino]-2-oxoethyl}-9H-pyrido[3,4-b] indole-3-carboxylic acid-(1-methylethyl)-ester is mixed in 3 ml of methanol with 1 ml of aqueous 2N sodium hydroxide solution and held at 40° C. until the reaction is completed. Then, the reaction mixture is acidified with dilute hydrochloric acid, the precipitated reaction product is suctioned off, washed with water and diethyl ether and dried in a vacuum. 370 mg of 5-benzyloxy-4-methoxymethyl-9-{2-[N-methyl-N-benzyl-amino]-2-oxoethyl}-9H-pyrido-[3,4-b]indole-3-carboxylic acid (decomposition starting at 239°) is obtained.

IR=3400, 8060, 2950, 1645, 1610, 1480, 1365, 1290, 1105 cm$^{-1}$.

EXAMPLE 7

786 mg of 5-benzyloxy-4-methoxymethyl-9H-pyrido[3,4-b]indole-3-carboxylic acid-(1-methylethyl)-ester (1.95 mmol) is taken up in 50 ml of dry tetrahydrofuran and mixed for deprotonation with 482 mg of 80% sodium hydride suspension in oil (20 mmol). It is allowed to stir for 20 more minutes at room temperature, then 500 mg of 2-[N-ethyl-N-benzyl]-2-bromoacetamide (1.95 mmol)—dissolved in 10 ml of tetrahydrofuran—is added. It is stirred for 48 hours at room temperature, mixed with 5 ml of 2N aqueous hydrochloric acid and diluted with water. It is then extracted with dichloromethane, the solvent is drawn off in a vacuum, and the crude product that is obtained is recrystallized on ethyl acetate. 540 mg of 5-benzyloxy-4-methoxymethyl-9{2-[N-ethyl-N-benzyl-amino]-2-oxo-ethyl}9H-pyrido[3,4-b]indole-3-carboxylic acid-(1-methylethyl)-ester with a melting point of 142°–144° C. is obtained.

IR=2978, 1735, 1654, 1503, 1471, 1299, 1268, 1168, 1105 cm$^{-1}$.

EXAMPLE 8

300 mg of 5-benzyloxy-4-methoxymethyl-9-{2-[N-ethyl-N-benzyl-amino]-2-oxoethyl}-9H-pyrido[3,4-b]indole-3-carboxylic acid-(1-methylethyl-ester (0.5 mmol) is mixed in 2 ml of methanol with 1 ml of 2N aqueous sodium hydroxide solution and held at 40° C. until the reaction is completed. Then, the reaction mixture is acidified with dilute hydrochloric acid, and the precipitated product is suctioned off. It is washed with water and then with diethyl ether, dried in a vacuum, and 210 mg of 5-benzyloxy-4-methoxymethyl-9-{2-[N-ethyl-N-benzyl-amino]-2-oxoethyl}-9H-pyrido[3,4-b]-indole-3-carboxylic acid (decomposition starting from 242° C.) is obtained.

IR=3400, 2930, 1751, 1654, 1472, 1365, 1269, 1138 cm$^{-1}$.

EXAMPLE 9

1000 mg of 5-benzyloxy-4-methoxymethyl-9H-pyrido[3,4-b]indole-3-carboxylic acid-1-methylethyl-ester is introduced into 10 ml of dry tetrahydrofuran and deprotonated at 0° C. with 78 mg of sodium hydride (80% suspension in oil) (2.6 mmol). Then, it is stirred for 20 minutes at room temperature, mixed with 697 mg of N-phenyl-piperazino-bromoacetamide (2.4 mmol)—dissolved in 3 ml of tetrahydrofuran—stirred for 5 hours at room temperature, filtered on diatomaceous earth, and then the solvent is drawn off in a vacuum. The crude product that is obtained is chromatographed on diatomaceous earth with dichloromethane/diethyl ether, and 789 mg of 5-[(N-phenyl-piperazino-2-oxethyl]-9H-pyrido[3,4-b]indole-3-carboxylic acid-(1-methyl-ethyl)-ester with a melting point of 256.2° C. is obtained.

IR=2977, 1702, 1559, 1500, 1300, 1268, 1235, 1107 cm$^{-1}$.

EXAMPLE 10

700 mg of 5-benzyloxy-4-methoxymethyl-9-[(N-phenyl-piperazino)-2-oxoethyl]-9H-pyrido[3,4-b]indole-3-carboxylic acid-(1-methylethyl)-ester is mixed in 1 ml of methanol with 1 ml of aqueous 2N sodium hydroxide solution and held at 40° C. until the reaction is completed. Then, the reaction mixture is acidified with dilute hydrochloric acid, the precipitated yellow reaction product is suctioned off, washed with water and diethyl ether and dried in a vacuum. 530 mg of 5-benzyloxy-4-methoxymethyl-9-[([N-phenylpiperazino)-2-oxoethyl]-9H-pyrido[3,4-b]indole-3-carboxylic acid is obtained (decomposition at 219° C.).

IR=3400, 1680, 1530, 1468, 1380, 1345, 1290, 1235, 1105 cm$^{-1}$.

EXAMPLE 11

605 g of 5-benzyloxy-4-methoxymethyl-9H-pyrido[3,4-b]indole-3-carboxylic acid-(1-methyl-ethyl)-ester (1.5 mmol) is taken up in 10 ml of dry tetrahydrofuran and mixed for deprotonation with 48 mg of 80% sodium hydride suspension in oil (1.6 mmol). It is allowed to stir for 20 more minutes at room temperature, then 500 mg of 2-[N-(2-ethoxy-2-oxo-ethyl)-N-(benzyl)-]-2-bromoacetamide (1.5 mmol)—dissolved in 10 ml of tetrahydrofuran—is added. It is stirred for 5 hours at room temperature, mixed with 5 ml of 2N aqueous hydrochloric acid and diluted with water. It is then extracted with dichloromethane, the solvent is drawn off in a vacuum, and the crude product that is obtained is chromatographed on silica gel using dichloromethane/diethyl ether. 378 mg of 5-benzyloxy-4-methoxymethyl-9{2-[N-(2-ethoxy-2-oxo-ethyl)-N-(benzyl)-amino]-2-oxoethyl}9H-pyrido[3,4-b]indole-3-carboxylic acid-(1-methylethyl)-ester with a melting point of 122.4° C. is obtained.

IR=2979, 1745, 1654, 1469, 1299, 1105 cm$^{-1}$.

EXAMPLE 12

200 mg of 5-benzyloxy-4-methoxymethyl-9-{2-[N-(2-ethoxy-2-oxo-ethyl)-N-(benzyl)-amino]-2-oxoethyl}-9H-pyrido[3,4-b]indole- 3-carboxylic acid-(1-methylethyl)-ester (0.3 mmol) is mixed in 2 ml of methanol with 1 ml of 2N aqueous sodium hydroxide solution and held at 40° C. until the reaction is completed. Then, the reaction mixture is acidified with dilute hydrochloric acid, and the precipitated product is suctioned off. It is washed with water and then with diethyl ether, dried in a vacuum and 120 mg of 6-benzyloxy-4-methoxymethyl-9-{6-[N-carboxymethyl-N-(benzyl)-amino]-2-oxohexyl}-9H-pyrido[3,4-b]-indole-3-carboxylic acid is obtained as a yellow, amorphous powder (decomposition starting from 245° C. ).

IR=3400, 2992, 1664, 1577, 1497, 1453, 1364, 1138 cm$^{-1}$.

EXAMPLE 13

600 mg of 5-benzyloxy-4-methoxymethyl-9-{2-[N-methyl-N-(2-phenylethyl)-amino]-2-oxoethyl}-9H-pyrido[3,4-b]indole-3-carboxylic acid is mixed in 30 ml of dichloromethane and at 0° C. with 0.087 ml of thionyl chloride and then with 0.09 ml of dimethylformamide. The reaction mixture is allowed to stir for 12 hours at room temperature, then drawn off in a vacuum, mixed again with 30 ml of dichloromethane, and the solvent is drawn off again in a vacuum. The acid chloride that is thus obtained is taken up in dichloromethane, cooled to 0° C., and mixed with 1 ml of triethylamine and 2 ml of dimethylamine solution (33% in absolute ethanol). The reaction mixture is allowed to stand for 5 hours at room temperature, it is poured into water, mixed with saturated sodium chloride solution and extracted three times with 30 ml of dichloromethane each. The organic phase is dried on magnesium sulfate and concentrated by evaporation in a vacuum. The crude product that is obtained is chromatographed on a silica gel column with dichloromethane/ethanol. As a polar fraction, 210 mg of 6-benzyloxy-4-hydroxymethyl-9-{2-(N-methyl-N-(phenylethyl)-amino)-2-oxoethyl}-9H-pyrido[3,4-b]indole-3-carboxylic acid-dimethylamide is obtained as a colorless solid (decomposition starting from 235° C.).

IR=3440, 3340, 2930, 1 670, 1650, 1630, 1480, 1290, 1230, 1190 cm$^{-1}$ and as a nonpolar fraction, 210 mg of 6-benzyloxy-4-hydroxymethyl-9-{2-[N-methyl-N-(2-phenylethyl)-amino]-2-oxoethyl}-9H-pyrido[3,4-b]indole-3-carboxylic acid lactone is obtained as a colorless oil.

IR=1760, 1660, 1480, 1350, 1310, 1200 cm$^{-1}$.

EXAMPLE 14

54 mg of 6-benzyloxy-4-hydroxymethyl-9-{2-[N-methyl-N-(2-(phenylethyl)-amino]-2-oxoethyl}-9H-pyrido[3,4-b]indole-3-carboxylic acid-dimethylamide is mixed in 5 ml of dry tetrahydrofuran at 0° C. with 6 mg of 80% sodium hydride suspension in oil, stirred for 15 minutes, and then 19 mg of bromoacetic acid-t-butyl ester is added. It is stirred for 3 hours at room temperature, filtered, and the crude product that is obtained is purified by preparative thin-layer chromatography on a silica gel plate using hexane-ethyl acetate 1:1. The product that is obtained is taken up in 3 ml of methanol, mixed with 1 ml of 10% sodium hydroxide solution and allowed to stand for 12 hours at room temperature. Then, the reaction mixture is diluted with water, neutralized with dilute solution and extracted with ethyl acetate. The crude product that is obtained is purified with a preparative silica gel plate with hexane-ethyl acetate, and 13 mg of 6-benzyloxy-4-(carboxymethoxymethyl)-9-{2-[N-methyl-N-(2-phenylethyl)-amino]-2-oxoethyl}-9H-pyrido[3,4-b]indole-carboxylic acid is obtained.

IR=3400, 2940, 1730, 1660, 1640, 1480, 1400, 1290, 1230, 1190 cm$^{-1}$.

EXAMPLE 15 a) A solution of 1.72 g of N-methyl-N-phenyl-ethylamine in 18 ml of dichloromethane is added in drops to a solution of 1 g of bromoacetyl chloride in 3.7 ml of dichloromethane at −25° C. within one hour. It is stirred for another 15 minutes at −25° C., and the reaction mixture is poured into a mixture of 100 ml of dichloromethane and 10 ml of water. The organic phase is washed with dilute hydrochloric acid and then with water, dried on sodium sulfate and concentrated by evaporation in a vacuum. 1.9 g of N-methyl-N-2-phenylethyl-2-bromoacetamide is obtained as a crude product.

b) 2.1 g of 5-benzyloxy-4-methoxymethyl-9H-pyrido-[3,4-b]indole-3-carboxylic acid-(1-methylethyl)ester is added to a suspension of 168 mg of sodium hydride (80% in mineral oil) in 25 ml of tetrahydrofuran at 0° C., it is stirred for 10 minutes at 0° C., then mixed with a solution of 1.6 g of N-methyl-N-2-phenylethyl-2-bromoacetamide and stirred for 18 hours at 24° C. Then, it is suctioned off on Celite, concentrated by evaporation in a vacuum, and the residue is purified by chromatography on silica gel. 2.8 g of 5-benzyloxy-4-methoxymethyl-9-{2-[N-methyl-N-(2-phenylethyl)-amino]-2-oxoethyl}-9H-pyrido[3,4-b]indole-3-carboxylic acid-(1-methylethyl)-ester is obtained as weak, yellowish crystals with a melting point of 146°–147° C.

IR=2980, 2930, 1720, 1660, 1650, 1512, 1580, 1100 cm$^{-1}$.

EXAMPLE 16

120 ml of an aqueous 0.5N lithium hydroxide solution is added to a solution of 7 g of the isopropylester, produced according to Example 1, in 120 ml of ethanol and 120 ml of tetrahydrofuran, and it is stirred for 6 hours at 60° C. under argon. Then, it is cooled to 20° C. and acidified to pH 3 with a 10% sulfuric acid solution. It is diluted with ethyl acetate, shaken with brine, dried with Na$_2$SO$_4$ and concentrated by evaporation in a vacuum. The solid residue is crystallized from an ethanol/diethyl ether mixture. In this case, 5 g of 5-benzyloxy-4-methoxymethyl-9-{2-[N-methyl-N-(2-phenethyl)amino]-2-oxyethyl}-β-carboline-3-carboxylic acid is obtained as pale yellow-colored crystals with a melting point of 167°–175° C.

IR (KBr): 3430, 2930, 1750, 1660, 1615, 1103 cm$^{-1}$.

EXAMPLE 17

0.035 ml of an aqueous solution of 822.5 mg of trishydroxymethyl-aminomethane in 1.5 ml of water is added to a solution of 100 mg of 5-benzyloxy-4-methoxymethyl-9-{2-[N-methyl-N-( 2-phenylethyl)-amino]-2-oxoethyl}-9H-pyrido[3,4-b]indole-3-carboxylic acid in 11 ml of acetonitrile at 80° C., it is stirred for one hour at 80° C., for one hour at 55° C., 3 hours at 45° C. and 48 hours at 24° C. The precipitated crystals are suctioned off, they are washed with a little acetonitrile, dried in a vacuum, and 130 mg of the trishydroxymethyl-aminomethane salt of 5-benzyloxy-4-methoxymethyl-9-{2-[N-methyl-N-(2-phenylethyl)-amino]-2-oxoethyl}-9H-pyrido-[3,4-b]indole-3-carboxylic acid is obtained as colorless crystals with a melting point of 171°–179° C.

EXAMPLE 18

9.9 mg of cyclohexylamine is added to a solution of 54 mg of 5-benzyloxy-4-methoxymethyl-9-{2-[N-methyl-N-(2-phenylethyl)-amino]-2-oxoethyl}-9H-pyrido[3,4-b]indole-3-carboxylic acid in 2 ml of acetonitrile and 0.5 ml of tetrahydrofuran at 80° C., it is stirred for one hour at 80° C., for one hour at 55° C., for three hours at 45° C. and for 48 hours at 22° C. The precipitated crystals are suctioned off, washed with a little acetonitrile, it is dried in a vacuum, and 55 mg of the cyclohexyl salt of 5-benzyloxy-4-methoxymethyl-9-{2-[N-methyl-N-(2-phenylethyl)-amino]-2-oxoethyl}-9H-pyrido-[3,4-b]indole-3 carboxylic acid is obtained as colorless crystals with a melting point of 164°–179° C.

EXAMPLE 19

4.4 g of 4-methoxymethyl-5-(4-nitrophenoxy)-9H-pyrido[3,4-b]indole-3-carboxylic acid-(1-methylethyl)-ester is added to a suspension of 315 mg of sodium hydride (80% suspension in mineral oil) and 50 ml of tetrahydrofuran at 0° C., it is stirred for 15 minutes at 0° C., then mixed with a solution of 3.1 g of N-methyl-N-2-phenylethyl-2-bromoacetamide in 10 ml of tetrahydrofuran and stirred for 20 hours at 24° C.

Then, it is filtered on Celite, the filtrate is concentrated by evaporation in a vacuum, and the crude product that is obtained is purified by chromatography on a silica gel column with ethyl acetate. 2.9 g of 4-methoxymethyl-5-(4-nitrophenoxy)-9-{2-[N-methyl-N-(2-phenylethyl)-amino]-2-oxoethyl}-9H-pyrido[3,4-b]indole-3-carboxylic acid-(1-methylethyl)-ester, which has a melting point of 187°–188° C. after recrystallization from ethanol/tetrahydrofuran, is obtained.

IR=2980, 2930, 1720, 1700, 1663, 1630, 1340, 1110 cm$^{-1}$.

EXAMPLE 20

10 ml of an aqueous 0.5N lithium hydroxide solution is added to a solution of 610 mg of 4-methoxymethyl-5-(4-nitrophenoxy)-9-{2-[N-methyl-N-(2-phenylethyl)-amino]-2-oxoethyl}-9H-pyrido[3,4-b]indole-3-carboxylic acid (1-methyl-ethyl)-ester in 10 ml of methanol and 10 ml of tetrahydrofuran, and it is stirred for 24 hours at 50° C. Then, it is cooled to 20° C., acidified with 10% aqueous sulfuric acid and diluted with ethyl acetate. The solution that is obtained is washed twice with saturated sodium chloride solution dried on sodium sulfate and evaporated to dryness in a vacuum. The crude product that is obtained is recrystallized from ethanol/tetrahydrofuran, and 360 mg of 4-methoxymethyl-5-(4-nitrophenoxy)-9-{2-[N-methyl-N-(2-phenylethyl)-amino]-2-oxoethyl}-9H-pyrido[3,4-b]indole-3-carboxylic acid is obtained as pale yellowish crystals with a melting point of 231°–232° C.

IR=3420, 2930, 1748, 1650, 1620, 1610, 1340, 1250 cm$^{-1}$.

EXAMPLE 21 a) 200 mg of 5-benzyloxy-4-methoxymethyl-9-{2-[N-methyl-N-(2-phenylethyl)-amino]-2-oxoethyl}-9H-pyrido[3,4-b]indole-3-carboxylic acid-(1-methylethyl)-ester is dissolved in 3 ml of tetrahydrofuran. Then, 0.29 ml of a 1.2 molar solution of diisobutylaluminum hydride in toluene is added in drops to the solution at 0° C., and it is stirred for 30 minutes at 0° C. Then, the reaction mixture is mixed with 0.1 ml of isopropanol and then with 0.1 ml of water, it is stirred for 2 hours at room temperature, filtered, and the filtrate is concentrated by evaporation in a vacuum. The residue is recrystallized from ethyl acetate, and 43 mg of 5-benzyloxy-4-methoxymethyl-9-{2-[N-methyl-N-(2-phenylethyl)-amino]-2-oxoethyl}-9H-pyrido[3,4-b]indole-3-carbaldehyde is obtained as colorless crystals with a melting point of 192°–197° C.

IR=2935, 2720, 1695, 1655, 1615, 1570, 1103 cm$^{-1}$.

b) 25 mg of sodium borohydride is added to a solution of 35 mg of 5-benzyloxy-4-methoxymethyl-9-{2-[N-methyl-N-(2-phenylethyl)-amino]-2-oxoethyl}-9H-pyrido[3,4-b]indole-3-carbaldehyde in 1 ml of tetrahydrofuran at 0° C., and it is then stirred for 3 hours at 0° C. Then, the reaction mixture is poured into ice water and extracted three times with ethyl acetate. The organic phase is dried on magnesium sulfate, filtered and concentrated by evaporation in a vacuum. 34 mg of 5-benzyloxy-3-hydroxymethyl-4-methoxymethyl-9-{2-[N-methyl-N-(2-phenylethyl)-amino]-2-oxoethyl}-9H-pyrido[3,4-b]indole is obtained.

IR=3360, 2939, 1665, 1580, 1466, 126, 1101 cm$^{-1}$.

EXAMPLE 22

404.5 mg of 5-benzyloxy-4-methoxymethyl-9H-pyrido[3,4-b]indole-3-carboxylic acid-(1-methylethyl)-ester (1 mmol) is dissolved in 20 ml of dimethylformamide, mixed with 597 mg of 3-phenylpropyl bromide and 40 mg of sodium hydride (60% suspension in oil), and it is stirred for one hour at room temperature. 300 ml of methyl-tert-butyl ether is added to the reaction mixture, and the organic phase is washed with 20% citric acid and saturated sodium chloride solution. The organic phase is dried on sodium sulfate and evaporated to dryness in a vacuum. The crude product that is obtained is purified on a silica gel column with ethyl acetate-hexane, and 338 mg of 5-benzyloxy-4-methoxymethyl-9-(3-phenylpropyl)-9H-pyrido[3,4-b]indole-3-carboxylic acid-(1-methylethyl)-ether is obtained.

IR=2980, 2940, 1730, 1615, 1580, 1500, 1460, 1300, 1265, 1160, 1100 cm$^{-1}$.

EXAMPLE 23

Under the conditions of Example 2, 314 mg of 5-benzyloxy-4-methoxymethyl-9-(3-phenylpropyl)-9H-pyrido[3,4-b]indole-3 -carboxylic acid-(1-methylethyl)-ester is saponified, worked up, and recrystallization from ethanol, 262 mg of 5-benzyloxy-4-methoxymethyl-9-(3-phenylpropyl)-9H-pyrido[3,4-b]indole-3-carboxylic acid with a melting point of 132° C. is obtained.

IR=3600, 3100, 2930, 1745, 1655, 1625, 1610, 1575, 1495, 1450, 1270 cm$^{-1}$.

EXAMPLE 24

10 mg of an 80% suspension of sodium hydride in oil is mixed with 10 ml of tetrahydrofuran and to 0° C. 404.5 mg of 5-benzyloxy-4-methoxymethyl-9H-pyrido[3,4-b]indole-3-carboxylic acid-(1-methylethyl)-ester is added to the suspension, it is stirred for 10 minutes at 0° C., mixed with 406 mg of 6-(4-methoxyphenyl)-hexyl bromide, and the reaction mixture is stirred for 16 hours at room temperature. After the reaction mixture is worked up as described, 330 mg of 5-benzyloxy-4-methoxymethyl-9-[6-(4-methoxyphenyl)-hexyl]-9H-pyrido[3,4-b]indole-3-carboxylic acid-(1-methylethyl)-ester is obtained.

EXAMPLE 25

A solution of 1.096 g of 5-benzyloxy-4-methyl-9H-pyrido[3,4-b]indole-3-carboxylic acid-(1-methylethyl)-ester (2.93 mmol) in 2.9 ml of tetrahydrofuran is added to a suspension of 92.2 mg of sodium hydride (3.03 mmol; 80% in mineral oil) at 0° C. under nitrogen, and it is stirred for 10 minutes at 0° C. Then, 750 mg (2.93 mmol) of N-methyl-N-phenylethyl-2-bromoacetamide is added, and it is then stirred for 18 hours at 24° C. It is filtered off on Celite, the filtrate is concentrated by evaporation in a vacuum, and the crude product that is thus obtained is purified on a silica gel column with hexane/0–100% ethyl acetate. In this way, 1.24 g of 5-benzyloxy-4-methyl-9-(2-[N-methyl-N-(2-phenylethyl)-amino]-2-oxoethyl)-9H-pyrido[3,4-b]indole-3-carboxylic acid-(1-methylethyl)-ester is obtained as an amorphous, yellowish-colored solid with a melting point of 69°–74° C.

IR=2980, 2935, 1718, 1665, 1630, 1580, 1468, 1303, 1268, 995 cm$^{-1}$.

EXAMPLE 26

5.5 ml of a 0.5N lithium hydroxide solution is added to a solution of 300 mg (0.546 mmol) of the ester, produced according to Example 25, in 11 ml of a mixture of methanol and tetrahydrofuran at a 1:1 ratio. After 18 hours of stirring at 24° C., the reaction mixture is acidified with a 1N hydrochloric acid solution to pH 4, saturated with sodium chloride and extracted three times with 100 ml of tetrahydrofuran each. The combined organic phases are dried on sodium sulfate and concentrated by evaporation after filtration in a vacuum. The crude product that is thus obtained is recrystallized from tetrahydrofuran. In this way, 155.2 mg of 5-benzyloxy-4-methyl-9-{2-(N-methyl-N-(2-phenylethylamino]-2-oxoethyl}-9H-pyrido[3,4-b]indole-3-carboxylic acid is obtained as yellowish-colored crystals with a melting point of 136° C.

IR=3430, 2938, 1743, 1660, 1628, 1605, 1493, 1370, 1275, 990 cm$^{-1}$.

EXAMPLE 27

404.5 mg of 5-benzyloxy-4-methoxymethyl-9H-pyrido[3,4-b]indole-3-carboxylic acid-(1-methylethyl)-ester (1 mmol) is dissolved in 15 ml of dimethylformamide and mixed with 217 mg (1.1 mmol) of cinnamyl bromide and 358 mg (1.1 mmol) of cesium carbonate. It is stirred for 48 hours at room temperature, the reaction mixture is worked up, as described in Example 26, and after chromatography, 210 mg of 5-benzyloxy-4-methoxymethyl-9-cinnamoyl-9H-pyrido[3,4-b]indole-3-carboxylic acid-(1-methylethyl)-ester is obtained.

IR(Film): 2979, 2932, 1732, 1613, 1578, 1499, 1463, 1371, 1298, 1267, 1242, 1162, 1108, 1049, 966, 785, 730, 697 $cm^{-1}$.

EXAMPLE 28

200 mg (0.384 mmol) of the compound that is presented according to Example 27 is added to 10 ml of methanol and mixed with 10 ml of a mixture of KOH, MeOH and $H_2O$. After stirring overnight at 50° C., starting material is still present. Another 5 ml of the mixture is added, and the batch is stirred over the weekend at 50° C. The reaction mixture is diluted with 30 ml of water, and the methanol is concentrated by evaporation. The aqueous phase is acidified to pH 4 with 10% $H_2SO_4$. After 10 minutes of stirring, the precipitated product is suctioned off, washed with water and dried in a vacuum in a drying oven at 50° C. 147 mg of yellow crystals (80%), melting point 110°–112° C.

IR(KBr): 3700-3120, 3120-2200, 3030, 2930, 1747, 1629, 1610, 1578, 1497, 1465, 1455, 1365, 1345, 1270, 1160, 1108, 968, 787, 750, 697 $cm^{-1}$.

EXAMPLE 29

404.5 mg of 5-benzyloxy-4-methoxymethyl-9H-pyrido[3,4-b]indole-3-carboxylic acid-(1-methylethyl)-ester (1 mmol) is dissolved in 15 ml of dimethylformamide and mixed with 188 mg (1.1 mmol) of benzyl bromide and 358 mg of cesium carbonate. It is stirred for 48 hours at room temperature, the reaction mixture s worked up as described in Example 26, and after chromatography, 194 mg of 5-benzyloxy-4-methoxymethyl-9-benzyl-9H-pyrido[3,4-b]indole-3-carboxylic acid-(1-methylethyl)-ester is obtained.

IR(KBr)=2973, 2930, 1710, 1615, 1578, 1500, 1498, 1463, 1450, 1361, 1270, 1210, 1195, 1100, 1057, 1000, 750 $cm^{-1}$.

EXAMPLE 30

174 mg (0.352 mmol) of the compound that is presented according to Example 29 is reacted as described in Example 27 and worked up. 137 mg of yellow crystals (86%). Melting point 170°–172° C.

IR(KBr)=3700-3100, 3100-2300, 3030, 2930, 1745, 1625, 1610, 1575, 1495, 1450, 1365, 1345, 1270, 1160, 1100, 1000, 785, 730, 697 $cm^{-1}$.

We claim:

1. A 9H-Pyrido[3,4-b]indole compound of formula I

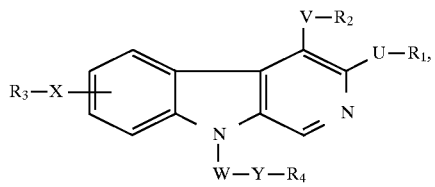

in which

U, V and W mean a single bond or a $C_1$–$C_6$ alkylene group, $R_1$ represents a hydrogen atom, a hydroxy group or a carboxyl group, and $R_2$ is a hydrogen atom, a hydroxy group, a $C_1$–$C_4$ alkoxy group, a $C_1$–$C_6$ alkanoyloxy group or a $C_1$–$C_4$-ω-carboxyalkoxy group, or $R_1$ and $R_2$ together are an oxycarbonyl group, X means a single bond or an oxygen atom, Y means a single bond, the grouping —CONR with R being a hydrogen atom or a $C_1$–$C_7$ alkyl group that is optionally substituted by a carboxyl group, or the grouping

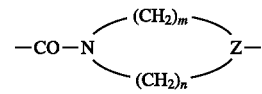

with m and n having numbers of a total of 3, 4 or 5, and Z meaning a methylidine group or an aza group, $R_3$ and $R_4$ in each case is a phenyl group optionally substituted by halogen atoms, trifluoromethyl groups, $C_1$–$C_7$ alkyl groups, $C_1$–$C_4$ alkoxy groups, carboxyl groups and/or nitro groups; a $C_1$–$C_4$ alkylenephenyl group or a naphthyl group, or a carboxylic acid of formula I, or an ester of physiologically harmless alcohol, or an amide of physiologically tolerable amine or a salt of physiologically compatible base, with the proviso that where W is a single bond, Y is not —$CONR^1$.

2. A compound according to claim 1, wherein W is a $C_{1-6}$-alkylene group.

3. A pharmaceutical composition, comprising a 9H-pyrido-[3,4-b]indole compound of formula I according to claim 1, and a physiologically acceptable carrier.

4. A process for the production of a 9H-pyrido[3,4-b]indole compound of formula I according to claim 1, comprising alkylating a 9H-pyrido[3,4-b]indole compound of formula II

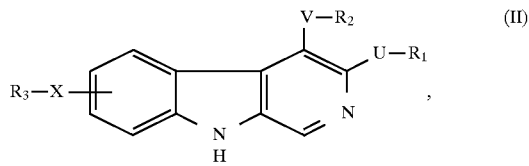

in which

U, V, X, $R_1$, $R_2$ and $R_3$ have the meaning mentioned in claim 1, with a reactive compound of formula III

Q—W—Y—$R_4$ (III), in which W, Y and $R_4$ have the meaning mentioned in claim 1 and Q symbolizes a nucleofuge radical, and optionally converting the compounds that into their esters, amides or salts.

* * * * *